US006616623B1

(12) United States Patent
Kutushov (10) Patent No.: US 6,616,623 B1
(45) Date of Patent: Sep. 9, 2003

(54) SYSTEM FOR CORRECTION OF A BIOLOGICAL FLUID

(75) Inventor: Michael Kutushov, Petach Tikva (IL)

(73) Assignee: Idializa Ltd., Ramat Hasharon (IL)

( * ) Notice: Subject to any disclaimer, the term of this patent is extended or adjusted under 35 U.S.C. 154(b) by 0 days.

(21) Appl. No.: 09/411,375

(22) Filed: Oct. 4, 1999

Related U.S. Application Data (63) Continuation of application No. 08/887,326, filed on Jul. 2, 1997, now Pat. No. 5,980,479.

(51) Int. Cl.$^7$ .................. A61M 37/00; C02F 1/48; B01D 35/06
(52) U.S. Cl. ............ 604/6.09; 604/4.01; 604/5.04; 210/222; 210/223; 210/695
(58) Field of Search .............. 604/4.01, 5.01, 604/5.02, 5.03, 5.04, 8, 9, 10, 6.09; 210/222, 223, 695

(56) References Cited

U.S. PATENT DOCUMENTS

| | | | | |
|---|---|---|---|---|
| 3,676,337 A | * | 7/1972 | Kolm ............. | 118/502 |
| 4,663,029 A | * | 5/1987 | Kelland et al. ....... | 209/214 |
| 5,084,011 A | * | 1/1992 | Grady ............ | 604/24 |
| 5,123,901 A | * | 6/1992 | Carew ............ | 604/5 |
| 5,439,586 A | | 8/1995 | Richards et al. | |
| 5,449,342 A | * | 9/1995 | Hirose et al. ........ | 600/16 |
| 5,466,574 A | * | 11/1995 | Liberti et al. ....... | 435/5 |
| 5,510,716 A | * | 4/1996 | Buffaloe et al. ...... | 210/646 |
| 5,536,475 A | * | 7/1996 | Moubayed et al. ...... | 422/101 |
| 5,628,407 A | * | 5/1997 | Gilbert et al. ....... | 209/214 |
| 5,711,871 A | * | 1/1998 | Miltenyi ........... | 210/86 |
| 6,036,857 A | * | 3/2000 | Chen et al. ......... | 210/222 |
| 6,139,736 A | * | 10/2000 | Inaba ............. | 210/222 |
| 6,231,760 B1 | * | 5/2001 | Siddiqi ............ | 210/222 |
| 6,264,842 B1 | * | 7/2001 | Boehm ............. | 210/695 |

FOREIGN PATENT DOCUMENTS

WO    WO 94/21310    9/1994

OTHER PUBLICATIONS

Database WPI; XP002137958; Section PQ, Week 199517; Derwent Publications Ltd., AN 1995–129933; 1993.
Database WPI; XP002137959; Section Ch, Week 199435; Derwent Publications Ltd., AN 1994–284101; 1994.

* cited by examiner

Primary Examiner—Angela D. Sykes
Assistant Examiner—Leslie Deak
(74) Attorney, Agent, or Firm—Browdy and Neimark, P.L.L.C.

(57) ABSTRACT

A system is presented for correction of a patient's biological fluid, such as his blood, lymph or spinal fluid, containing various low-, medium- and high-molecular toxins. The system comprises an extracorporeal flow line in the form of a flexible tube interconnected between outlet and inlet means attached to appropriate location(s) on a patient's body. A small amount of the biological fluid, i.e., substantially not exceeding 100 ml, substantially continuously flows through the tube, and is mixed with magneto-conductive particles capable of adsorbing the various toxins. An obtained mixture of the biological fluid with the particles passes through a magnetic field region, and substantially all of the magneto-conductive particles are retained therein. Particle-free biological fluid is then returned into the patient's body through the inlet means.

63 Claims, 5 Drawing Sheets

SYSTEM FOR CORRECTION OF A BIOLOGICAL FLUID

This application is a continuation of parent application No. 08/887,326, filed Jul. 2, 1997 now U.S. Pat. No. 5,980,479.

FIELD OF THE INVENTION

The present invention is generally in the field of magnetic separation techniques and relates to a system for the correction of a biological fluid, such as blood, lymph and spinal fluid.

BACKGROUND OF TEE INVENTION

Methods of blood correction are known and widely used in particular for treatment in patients suffering from kidney and/or liver diseases. One of the conventional techniques, known as haemo- or lymph-perfusion, is based on passing blood or lymph fluid through an adsorbent such as granular activated carbon. Unfortunately, a relatively large amount of biological fluid, namely about 250–300 ml needs to be withdrawn from the patient's body at any given time, and the entire system is cumbersome. Furthermore, the carbon loses its effectiveness after 15–20 minutes from the beginning of the treatment because it slimes and, owing to the relatively large dimensions of the carbon particles, becomes formed with numerous channels formed therein by the blood passage therethrough. As a result, unpurified blood returns into the body.

Another conventional technique, known as haemodialysis, is based on the use of semipermeable membranes. Similarly to the haemoperfusion, this method also requires the withdrawal of about 400–600 ml of blood at any given time. The whole process of purification requires blood to circulate through the apparatus more than 5 times. Both of the above described techniques disturb the blood's rheology. That is to say they traumatize the erythrocytes and thrombocytcs. They also require bulky equipment.

Methods and devices for blood purification have been developed employing the so called haemoseparation technique which is based on the principles of magnetic separation. Generally, the magnetic separation procedure consists of retaining magnetic materials in a chamber disposed in a magnetic field. Systems of this kind typically provide mixing of the blood with a previously prepared magneto-conductive substance formed of paramagnetic beads having a coating which selectively binds a preselected pathogenic agent or endotoxin. Then, by passing a blood mixture containing the paramagnetic beads having the bound pathogenic agent through a magnetic field, the paramagnetic beads are magnetically separated from the blood.

U.S. Pat. No. 5,123,901 discloses a method and an apparatus for removing preselected cells or viruses from the blood. The blood is first tested for selecting a preselected pathogenic agent and identifying an associated antigenic agent. A composition is then prepared, such as an immunoglobulin or an antibody, for coating a plurality of paramagnetic beads with outer layers so as to recognize and bind selectively to the preselected pathogenic agent. The paramagnetic beads have a smooth surface in order to minimize the amount of antibody necessary to coat the beads. The blood is perfused into a flow line, and the coated paramagnetic beads are metered into the blood either before its entering a mixing coil, or thereafter. A received mixture of blood and paramagnetic beads/pathogenic agent complexes flows into a chamber of a magnetic separator. A graded magnetic field is provided along the length of the separation chamber, so as to adhere substantially all of the paramagnetic beads/pathogenic agent complexes to the separation chamber wall. However, both the mixing chamber and the separation chamber are bulky, namely each about 300 cm in length. About 600 to 700 ml of blood occupies the flow circuit at any given time, while the purging process is completed in approximately 6 to 10 hours of operation. Additionally, the magnetic field is graded such that it begins at 4000 Gauss (0.4 T) and increases to about 10000 Gauss (1 T), which is too much for such a biological fluid as blood. Indeed, it is known in the art that the magnetic field intensity which is suitable for intervention into a biological fluid is defined by the properties of the latter. This is more essential for such a multicomponent biological fluid as blood containing ethrocytes whose equidistance increases and membrane resistivity decreases with the increase of the magnetic field. As a result, the erythrocytes grow old and break.

PCT Publication No. WO 94/21310 discloses a method and an apparatus for correcting a biological fluid typically based on mixing the latter with a biocompatible suspension of a magneto-conductive composition within a mixing chamber, and, then, passing the obtained mixture through a filter disposed within a magnetic field. The biological fluid is corrected in a number of cycles. In order to provide more effective mixing, the mixing chamber is filled in with discrete doses of the biological fluid and the suspension of the magneto-conductive composition. The obtained mixture is left standing whilst being continuously mixed, and, then, each further dose is added to the previously obtained mixture. The resulting mixture than passes through a filter disposed in a magnetic field effect region. The time of passage of the mixture through the filter is preset so as to achieve an optimum effect in the magnetic field which does not exceed 120 mT. Unfortunately, such procedure is slow, requiring that about 100 ml of the biological fluid be withdrawn from the body during a cycle and resulting in about 10 hours of operation for the complete correction of the total amount of the patient's blood.

It should be noted that such parameters as the amount of biological fluid which is withdrawn from the patient's body at any given time and the duration of the whole treatment are very important and even determinant when dealing with endotoxic and/or exotoxic shocks which are usually caused by poisoning.

SUMMARY OF THE INVENTION

There is accordingly a need in the art to facilitate the purification of a biological fluid by providing a novel magnetic system for correcting a biological fluid, such as blood, lymph or spinal fluid, by removing therefrom various endotoxins and exotoxins.

It is a major feature of the present invention to provide such a device which is miniature and easy to construct, and requires a very small amount of biological fluid to be withdrawn from the patient's body.

There is thus provided according to a broad aspect of the present invention a system for correcting a patient's biological fluid containing various low-, medium- and high-molecular toxins, the system comprising:

(i) an outlet means for attaching to the patient's body for substantially continuously withdrawing therefrom the biological fluid containing the various toxins;

(ii) an inlet means for attaching to the patient's body for returning corrected biological fluid back into the patient's body;

(iii) an extracorporeal flow line interconnected between the outlet and inlet means for passing therethrough, in a substantially continuous flow, a predetermined amount of the biological fluid substantially not exceeding 100 ml, so as to be mixed with a plurality of magneto-conductive particles capable of adsorbing said toxins for obtaining a mixture of the biological fluid with said particles;

(iv) a magnetic mechanism comprising a magnetic field source producing a magnetic field region within a flow of said mixture for retaining said magneto-conductive particles in said region from a flow of particle-free biological fluid to be returned into the patient's body through the inlet means.

Preferably, the flow line is in the form of a flexible tube.

The magneto-conductive particles may be contained in a vessel coupled to the flow line through a pipe. To this end, the system comprises a feeding means for substantially continuously feeding the particles into and through the flow line. Preferably, the feeding means comprises a pump coupled to the vessel for supplying air thereto so as to provide an excessive pressure within the vessel.

Additionally, the system may also comprise a feeding means (e.g., a pump) for substantially continuously feeding the biological fluid containing various toxins into and through the flow line. The same pump, which may be of a peristaltic or piezoelectric type, may be employed for feeding both the magneto-conductive particles and the biological fluid.

Alternatively, the magneto-conductive particles may be located inside the flow line in a flow path of the biological fluid containing the various toxins. The flow line may include first and second flexible tubes and a sealed vessel. The magneto-conductive particles are accommodated within a bottom region of the vessel. The first tube is connected between the outlet means and the particles, while the second tube is connected between the inlet means and a top region of the vessel.

Preferably, the particles are contained in a suspension thereof. The suspension may be formed of either a blood substitute composition, physiological solution or the like allowed for intravenous injection.

If the biological fluid is blood, the outlet and inlet means are associated with the patient's artery and vein, or with two locations on his vein. If the biological fluid to be corrected is the patient's lymph, the outlet means includes a catheter implanted into the large pectoral lympheduct at the place of its falling into the cava, and the input means includes a catheter inserted into either jugular or cubital vein. If the patient's spinal fluid is to be corrected, the outlet means includes a needle inserted into the cistern through the cervical opening, and the inlet means includes a needle inserted between the $4^{th}$ and the $5^{th}$ lumbar vertebrae. Alternatively, a two-channel needle, installed either into the cistern through the cervical opening or into the spine between the $4^{th}$ and the $5^{th}$ lumbar vertebrae, can be used The magneto-conductive particles are formed of paramagnetic or ferromagnetic material, and may have prevailing hydrophilic or hydrophobic properties.

The system, preferably, also comprises a mixing means located in the flow path of the biological fluid containing the various toxins. The suing means may comprise a multi-threaded worm mechanism. Alternatively, the mixing means may comprise a magnetic mechanism having displaceable opposite magnetic poles.

The magnetic field source comprises at least one permanent magnet mounted outside the flow line and proximate thereto. The permanent magnet may be in the form of a substantially flat plate, or a ring surrounding the flow line. The opposite poles of the magnet may be connected by a cover plate formed of a magnetic soft material.

The magnetic mechanism may also comprise a wire wound on the outer surface of the flow line wit the magnetic field region. Additionally, or alternatively, the magnetic mechanism may comprise an adhering means accommodated inside the flow line for adhering thereon the magneto-conductive particles. Such an adhering means may be a paramagnetic or ferromagnetic filler element installed inside the flow line within the magnetic field effect region. The filler may be in the form of a loosely laid wire, e.g., a barbed wire. The wire may have a varying diameter and a varying laying density along the magnetic field region. It should be noted that the magnetic field source and the adhering means may be constituted by at least one permanent magnet accommodated inside the flow line.

The system also comprises a control means coupled to the flow line and to the magnetic mechanism for operating the same. Preferably, the control means includes a plurality of clamps accommodated along the flow line for regulating the flow of the biological fluid and a monitoring means for checking velocities of the flow of the biological fluid containing the various toxins, the mixture and the particle-free biological fluid.

If the biological fluid to be corrected is the patient's blood, the system preferably also comprises a filtering means for removing water from blood which may include at least one semipermeable membrane, or water adsorbent material formed of hydrolyzed starch polymer. The filtering means may be accommodated either in the flow path of blood containing the various toxins, or in the flow path of the particle-free blood. The magneto-conductive particles are formed with activated porous surfaces. The particles may be formed of iron, iron oxide, carbon coated iron, silicone coated iron, aluminum coated iron, dextran coated iron. Preferably, the magneto-conductive particles are further coated with a protective layer formed of protein or the patient's blood.

The advantages of the present invention are thus self-evident. The system according to the invention needs a very small amount of the biological fluid to be withdrawn from the patient's body at a given time. This is very important feature, because it, on the one hand, does not cause danger to the patient and, on the other hand, enables to make the system desirably miniature.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4b schematically illustrates the principles of operation of a magnetic mechanism suitable for the separation assembly of FIG. 4a;

DETAILED DESCRIPTION OF A PREFERRED EMBODIMENT

Figure 1:
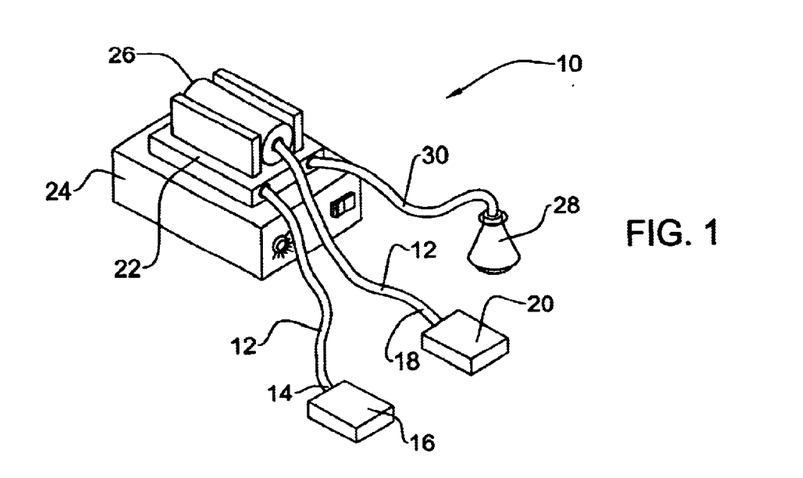
FIG. 1 is a pictorial illustration of the principal components of a system according to the invention.

Referring to FIG. 1, there is illustrated an extracorporeal system, generally designated 10, associated with a patient (not shown) for correcting his biological fluid (blood, lymph or spinal fluid). The system 10 comprises a flow line in the form of a flexible tube 12 made of silicon, polychlorvinyl or other bioinert materials. The tube 12 is coupled at its one end 14 to an outlet port 16 for withdrawing the biological fluid from the patient's body (e.g., his vein, in the case of blood correction), and by its opposite end 18, to an inlet port 20 for returning the corrected (purified) biological fluid into the patient's body (e.g., vein).

For the correction of the patient's lymph, the outlet port 16 includes a catheter implanted into the large pectoral lympheduct at the place of its falling into the cava, and the input port 20 includes a catheter inserted into either jugular or cubital vein. For the correction of the patient's spinal fluid, the outlet port 16 includes a needle inserted into the cistern through the cervical opening, and the inlet port 20 includes a needle inserted between the $4^{th}$ and the $5^{th}$ lumbar vertebrae. Alternatively, the outlet and inlet ports may be constituted by a two-channel needle, which is installed either into the cistern through the cervical opening or into the spine between the $4^{th}$ and the $5^{th}$ lumbar vertebrae. Needles can be replaced by plastic catheters.

As further shown in FIG. 1, a pump 22 is provided and operated by a motor 24 to create a substantially continuous flow of the biological fluid to and through the tube 12. The pump 22 may be of a peristaltic or a piezoelectric kind. The operation of the pump 22 enables to desirably adjust the speed of the fluid circulation through the tube 12, for example, within the range 1–10 ml/min for the lymph correction and 1–30ml/min for the spinal fluid correction.

It should be noted, although not specifically shown, that if the biological fluid to be corrected is the patient's lymph fluid, a certain amount of lymph can be first withdrawn into a sack, from which it is fed into the tube 12. In this case, the speed of lymph passage through the tube can be increased up to 100 ml/min.

It is understood that the speed of the fluid circulation through the tube 12, as well as the tube's dimensions, defines the amount of fluid continually withdrawn from the patient's body. For lymph, it is about 10–30 ml, and this parameter is less critical, as compared to that of the spinal fluid correction case, since the total amount of lymph existing in a human body is in the range 1.5–2.5l. For the correction of spinal fluid, the speed value and, consequently, the amount of spinal fluid continually withdrawn from the patient's body, are more important parameters, since the total amount of this fluid contained in the adult's body is about 150–300 ml, and in the child's body about 30–40 ml.

It should be noted that if the system 10 is used for correcting the patient's blood, and is the flow line is interconnected between the patient's artery and vein, there is no need for any pump means. The patient's blood is fed into and passes through the tube 12 due to a typically existing pressure difference between the artery and the vein. The blood thus flows through the flow line with its usual velocity of circulation within patient's body which is about 100–120 ml/min.

The system 10 is further provided with a separation assembly, generally designated 26, which is installed in the tube 12 so as to be in a flow path of the biological fluid. The construction and operation of the separation assembly 26 will be described more specifically further below with reference to FIGS. 4a and 4b. Further provided is a vessel 28, which contains a biocompatible magneto-conductive material (not shown), and is coupled to the tube 12 through a pipe 30. In this specific example of FIG. 1, the same pump 22 is used for substantially continuously feeding the magneto-conductive material from the vessel 28 into the tube 12.

The biocompatible magneto-conductive material is in the form of paramagnetic or ferromagnetic particles suspended within a liquid solution formed of any suitable biological fluid substitute composition or the like allowed for intravenous injection, such as gelatin (for blood or lymph correction), blood plasma, or physiological solution. When dealing with the spinal fluid, such a liquid solution may be a purified spinal fluid of the specific patient to be treated or synthetic composition biocompatible with the spinal fluid.

The particles are formed of one of the following materials: iron in its reduced form, so-called 'ferrum reductum'; iron oxide; carbon coated iron; dextran coated iron; silicone coated iron; aluminum coated iron; $Al_2SO_4$-coated iron; iron coated with ion-exchange resins (e.g., zirconium) with metal ions coupled thereto (to remove phosphor and phosphates); etc. Dispersed powders of 'ferrum reductum', iron oxide and carbon coated iron are obtainable either commercially, or by any suitable known technique. The aluminum and silicone coated iron particles may be obtained by the known plasma-chemical process, while the dextran coated iron particles—by the known technique of ultrasonic binding. The particles of either kind may, then, be specifically processed so as to have swelled, activated surfaces for possessing the following properties:

1) high adsorption capability due to their porous, irregular surface, rather than smooth, so as to provide a total porosity up to 2 $cm^3/g$ for being capable of adsorbing low-, medium- and high-molecular toxins contained in the biological fluid;

2) a specific surface area (per weight) of the whole magneto-conductive material up to 900–1300 $m^2/g$;

3) bulls weight of the particles characterizing their density is from 0.3 to 1.0 $g/cm^3$.

Preferably, the particle should have a substantially small size, i.e., about 0.01 $\mu$m 1 mm in the diameter, and its magnetization value should be about 130 to 200 emu/g, so as to be retained by a magnetic field due to its ponderomotive forces. The particles are bioinert to the biological fluid, i.e. non-toxic and non-corrosive. It is known in the art of adsorbing materials that density, total porousness and, therefore, total surface area are the most important factors defining efficiency of the adsorbing process. To this end, for example, maximum values of the total porousness and specific surface area of activated carbon used in the conventional haemo- or lymph-perfusion technique are about 1.11 $cm^3/g$ and 650 $m^2/g$, respectively.

It should be noted that such a magnetic particle could have a diamagnetic core and a magneto-sensitive coating. Optionally, the particles may be further coated by a protective and adsorbing coating formed of either protein of any known kind, particularly a food protein, or the patient's blood, so-called "auto-blood". Alternatively, or additionally, the iron particles may be coated by a selective coating, for example antibody, depending on a preselected pathogenic agent to be removed from the biological fluid. Moreover, the paramagnetic particle either coated or not may be further modified by antibiotics or similar medical compounds, e.g., polysaccharide.

It should also be noted that the provision of the suspension of the paramagnetic particles is optional solely for facilitating a flow of such particles through the flow line. The suspension may contain up to 90% of the paramagnetic particles.

Figure 2:
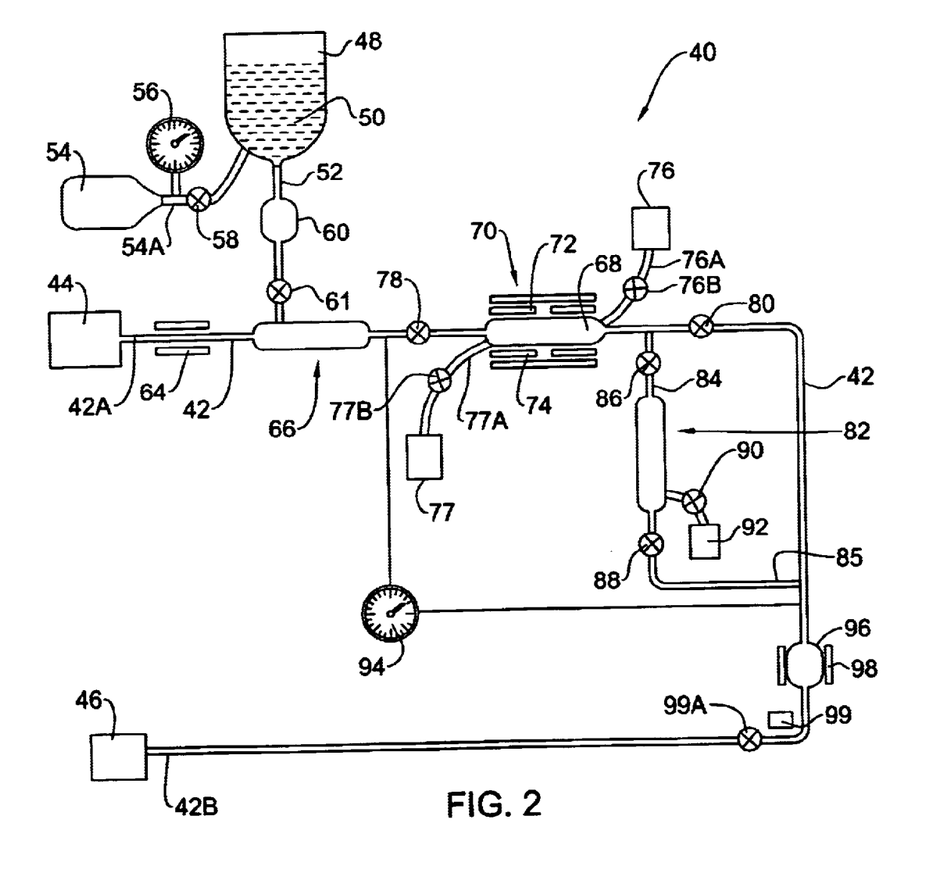
FIG. 2 is a schematic block diagram illustrating the main components of a system according to one embodiment of the invention.

Referring to FIG. 2 there is illustrated an extracorporeal system, generally denoted 40, for correcting the biological fluid circulating through the system. The system 40 similarly comprises a tube 42 connected at its opposite ends 42a and 42b to outlet and inlet ports 44 and 46, which are attached to the corresponding location(s) on the patient's body, as described above. A vessel 48 containing a biocompatible suspension of a magneto-conductive material 50 is coupled to the tube 42 through a pipe 52. A small pear-like pump 54 is connected to the vessel 48 through a pipe 54a for feeding air in a manner to provide excessive pressure within the vessel 48. This results in continuous supply of the suspension 50 into the tube 42. As shown, the air supply is controlled and regulated by a manometer 56 and a clamp 58. Such a pear-like pump can be replaced by any other suitable pump assembly. The flow of the suspension 50 into the tube 42 is, in turn, visually controlled and regulated by means of conventional dropper 60 and clamp 61 which are installed in the pipe 52.

Further and optionally provided is an electromagnet 64 mounted proximate to the outlet port 44, the purpose of which will be described further below. A mixing assembly 66 is optionally provided inside the tube 42 so as to be in the flow path of the biological fluid and of the suspension 50. A mixture, containing paramagnetic particles that have captured toxins and paramagnetic particles that may be free of toxins, and the biological fluid free of particles, is obtained inside the tube 42. The construction and operation of the mixing assembly 66 will be described further below with reference to FIG. 3.

Installed in the tube 42 is a separation assembly 68 having a magnetic mechanism 70. The separation assembly 68 is installed downstream of the mixing assembly 66, so as to be in the flow path of the obtained mixture. The magnetic mechanism 70 includes a pair of spaced-apart, parallel, permanent magnets 72 and 74 enclosing the assembly 68 therebetween for providing a magnetic field region thereinside and retaining the particles within that region. The construction and operation of the separation assembly 68 will be described more specifically further below with reference to FIGS. 4a and 4b.

A conventional injector 76 and a vessel 77 are coupled to the tube 42 through a pair of pipes 76a–77a and a pair of clamps 76b–77b, respectively, for cleaning the separation assembly 68 after use, so as to remove therefrom the particles retained by the magnetic field. To this end, additional clamps 78 and 80 are coupled to the tube 42 upstream and downstream of the assembly 68, respectively, so as to selectively connect and disconnect the latter from the flow line. It will be readily understood that the magnetic mechanism 70 is taken away from a vicinity of the separation assembly 68 for time (typically several seconds) needed for the process of cleaning.

Further and optionally provided is a filtering device 82, whose provision is needed for blood correction only, for removing water from the blood. As shown, the device 82 is coupled to the tube 42 through a pair of pipes 84 and 85 so as to be disposed in the flow path of the blood ensuing from the separation assembly 68. A clamps 86 and 88 are mounted on the pipes 84 and 85 and operated in a manner to selectively direct the blood into the filtering device 82. The operation of the device 82 is based on the principles of ultrafiltration consisting in that the blood, under an excessive pressure, passes through a plurality of parallel, tube-shaped, semipermeable membranes (not shown) extending along the flow path of the blood Thus, the blood, which is more viscous than water by approximately 5 times, passes along the membranes thereinside, while the water penetrates through the membranes. This technique is known per se and, therefore, need not be specifically described. Additional clamp 90 and vessel 92 are provided for gathering the separated water. Alternatively, although not specifically shown, the filtering device 82 may be accommodated upstream of the mixing assembly 66 so as to be in the flow path of the blood before it is mixed with the magneto-conductive material 50. It should be noted that the ultrafiltration may be replaced by another well known technique based on the use of water suitable adsorbent such as, for example, copolymer of hydrolyzed starch with polyakrylnitryl.

As further shown in FIG. 2, coupled to the tube 42 is an additional manometer 94 for controlling the velocities of both the mixture before entering the separation assembly 68 and the biological fluid ensuing therefrom. Installed in the tube 42 downstream of the separation assembly 68 is a trapper 96 comprising a magnetic mechanism 98, the purpose of which will be described further below. A sensor 99, either ultrasonic or optical, is mounted proximate to the tube 42 downstream of the trapper 96. The sensor 99 is capable of detecting the existence of any magnetic material in the biological fluid ensuing from the trapper 96. For this purpose, an additional clamp 99a is provided and operated by the sensor 99 for shutting off the passage of the biological fluid towards the inlet port 46, upon detecting the existence of the magnetic material in the biological fluid.

Figure 3:
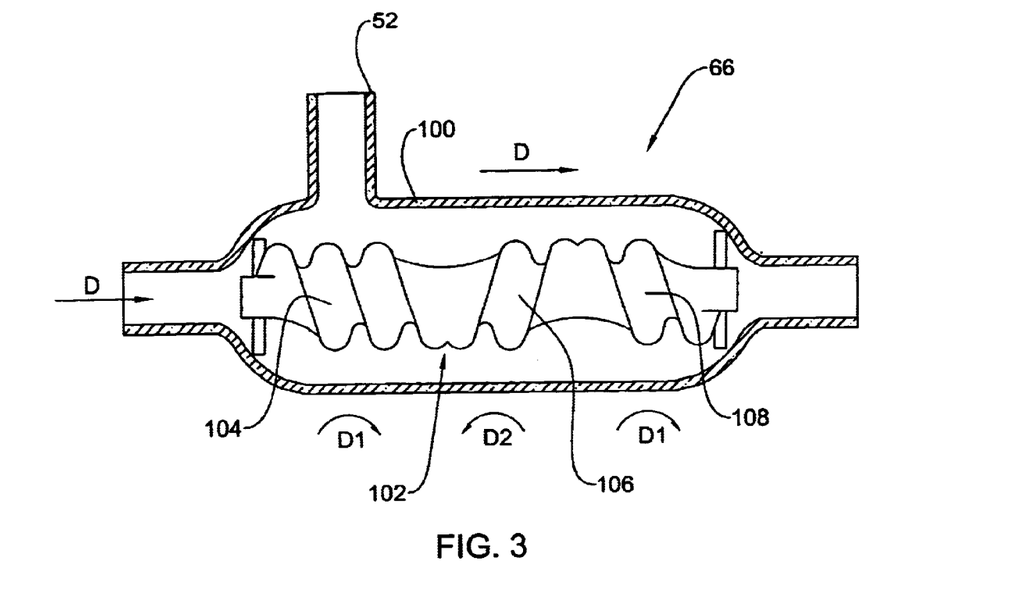
FIG. 3 is an exploded, partly cross-sectional view illustrating a mixing assembly suitable for the system of FIG. 2.

Turning now to FIG. 3, the mixing assembly 66 is optionally formed of a slightly thickened portion 100 of the tube 42, and a three-threaded worm mechanism 102 is mounted inside the portion 100. The mechanism 102 includes three worm elements 104, 106 and 108 which are either formed integrally or axially coupled. This construction of the worm mechanism 102 provides sequential rotation of the flow of biological fluid together with the suspension 50 in directions $D_1$, $D_2$ and $D_1$ during a progressive movement of the biological fluid and suspension through the portion 100 in a flow direction D. Thus, a mixture, containing the biological fluid and adsorptive and non-adsorptive paramagnetic particles, is provided without interrupting the continuous flow of the mixture. Obviously, such a multithreaded mechanism 102 may comprise more than three worm elements.

Figure 4A:
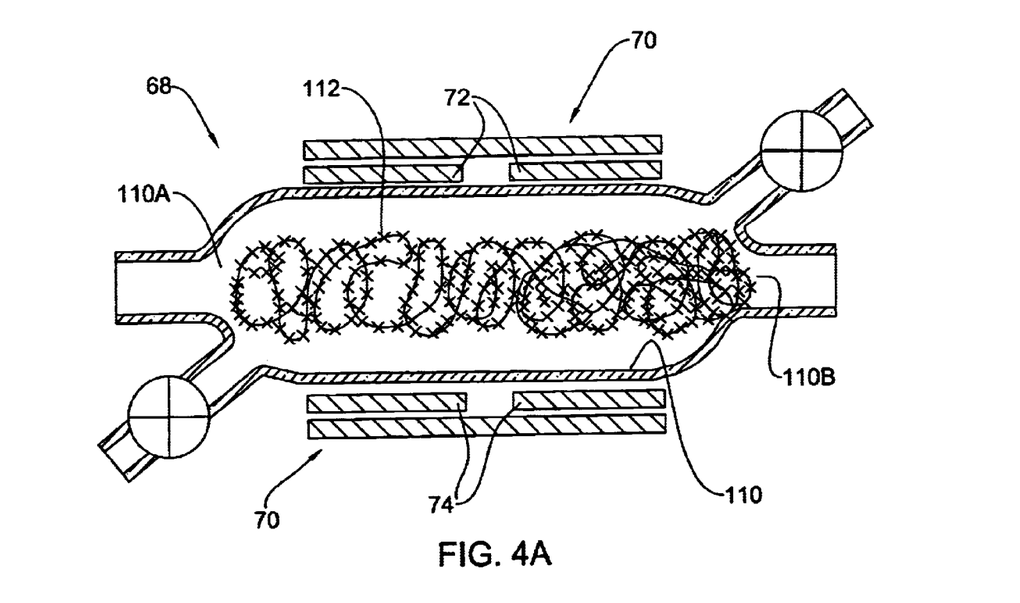
FIG. 4a is an exploded, partly cross-sectional illustration of a separation assembly suitable for the system of FIG. 2.

Reference is now made to FIG. 4a more specifically illustrating the separation assembly 68. In the present example, the separation assembly 68 is in the form of slightly thickened portion 110 of the tube 42, but this design is optional The portion 110 has its front and rear ends 110a and 110b, respectively, and has an approximate diameter of 20 mm in its inner center region. A barbed wire 112 is accommodated in the portion 110 in such a manner, that a total volume of the wire is approximately 10–50% of the volume of the portion 110. The wire 112 is made of a paramagnetic or ferromagnetic material such as, for example, permendur. As clearly shown, the wire 112 is loosely laid inside the portion 110 in such a manner that its laying density at the front end 110a of the portion 110 is less than that of the rear end 110*b*. Additionally, although not specifically shown, a diameter of the wire 112 decreases from approximately 0.5 mm at the front end 110*a* to approximately 0.05 mm at the rear end 110*b* of the portion 110. The wire 112 is coated with a bioinert material (not shown) such as, for example, silicone.

Figure 4B:
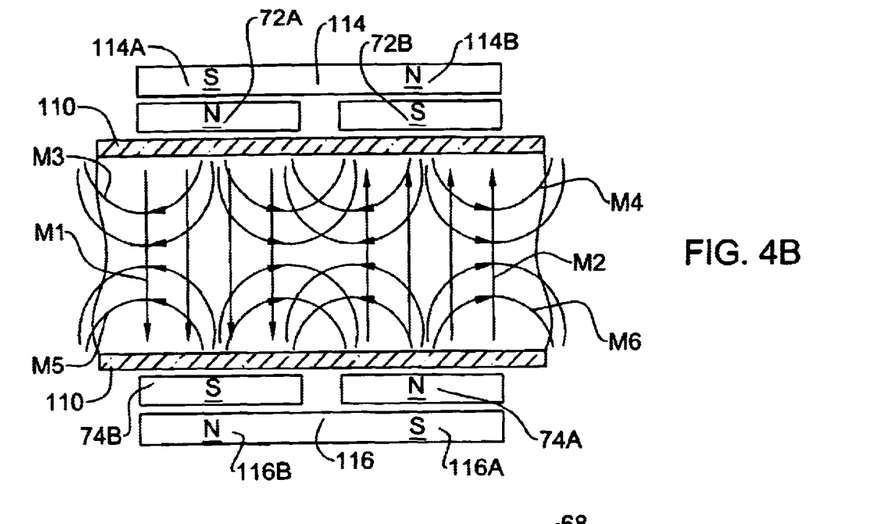

Referring to FIG. 4*b*, the magnets 72 and 74 are disposed in such a manner that north and south poles 72*a* and 72*b* of the magnet 72 oppose south and north poles 74*b* and 74*a* of the magnet 74, respectively. The poles 72*a* and 74*b* provides a magnetic field direction $M_1$, while the poles 72*b* and 74*a* provide a magnetic field of an opposite direction $M_2$. The opposite poles of the magnets are coupled by a pair of metal plates 114 and 116, respectively, formed of a magnetic soft material such as, for example, steel. It will be readily understood that additional magnetic poles 114*a*–114*b* and 116*a*–116*b* are, therefore, formed in the plates 114 and 116 which generate magnetic fields directions $M_3$, $M_4$, $M_5$ and $M_6$ inside the portion 110.

Figure 4C:
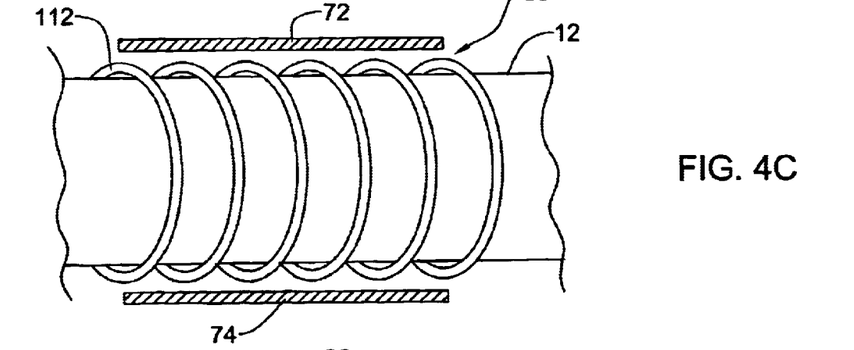
FIG. 4c illustrates an example of implementation of the magnetic mechanism to be used in the separation assembly.

FIG. 4*c* exemplifies another suitable implementation of the magnetic mechanism to be used in the separation assembly 68. Here, a metal wire is wound on the outer surface of the corresponding portion of the tube 12, rather than being installed thereinside.

Thus, owing to the provision of the plates 114 and 116, a flux density of the total magnetic field inside the portion 110 increases. Furthermore, on the one hand, such a paramagnetic wire 112 provides a high gradient of the magnetic field in a direction transverse to the flow direction D inside the portion 110, and, on the other hand, such a varying diameter of the wire 112 provides a high gradient of the magnetic field along the flow direction D. The wire 112 itself constitutes a physical retainer for preventing the paramagnetic particles from flowing out of the portion 110. The provision of such a varying laying density of the wire 112 as described above enables to obtain an even distribution of retained particles so as not to impede the flow of the mixture through the portion 110. Moreover, the provision of such a barbed wire enables the gradient of the magnetic field inside the portion 110 to be further increased.

If the system is used for blood correction, the provision of high gradient of the magnetic field enables the use of a relatively weak magnetic field, e.g., about 30–100 mT. This magnetic field is effective enough for separating substantially all the paramagnetic particles from the blood-particles mixture. As indicated above, it is a very important feature for the correction of blood that contains erythrocytes whose equidistance increases and membrane resistivity decreases with the increase of the magnetic field.

When dealing with the lymph correction, the magnetic field induction may be in the range of 1–1000 mT. This magnetic field is also suitable for the correction of spinal fluid, but for this purposes the value of the magnetic field is of less importance, and, generally, may be of any other value. Generally, the effective magnetic field induction to be created in the magnetic field region is determined by the speed of biological fluid passing through the separation assembly, which speed is, in turn, defined by the viscosity of the biological fluid to be corrected.

Alternatively, although not specifically shown, at least one permanent magnet, which is preferably planar, may be installed inside the portion 110 serving, thereby, for both generating the magnetic field and retaining the paramagnetic particles adhering on the magnet. Additionally, each of the horseshoe magnets 72 and 74 may be replaced by one or more flat- or ring-shaped permanent magnets.

Figure 5:
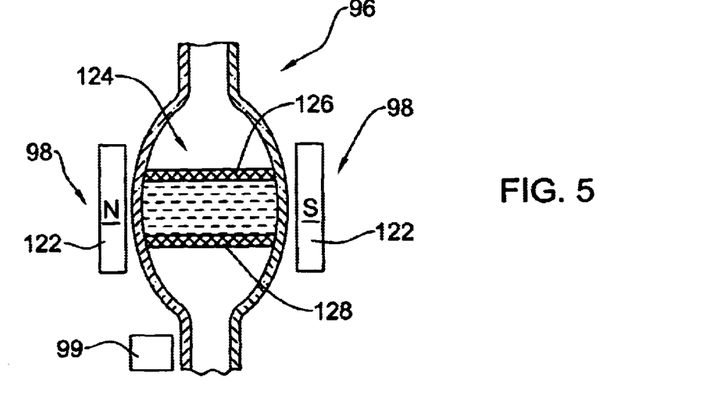
FIG. 5 is an exploded, partly cross-sectional illustration of a trapper suitable for the system of FIG. 2.

Turning now to FIG. 5, the trapper 96 is optionally formed of a slightly thickened portion 120 of the tube 42. The magnetic mechanism 98 comprises a permanent magnet 122, for example a horseshoe, mounted proximate to the portion 120 in a manner to enclose the latter between its opposite poles. A filler element, generally designated 124, is installed inside the portion 120. The element 124 includes a pair of spaced parallel lattices 126 and 128, the space between the lattices being filled in by particles formed of activated carbon. Alternatively, the filler element 124 may be designed like a single lattice, or a wire formed of paramagnetic or ferromagnetic material, for example such as the wire 112. Thus, the magnet 122 provides a magnetic field region within the portion 120.

The system 40 operates in the following manner. A suitable amount of biological fluid (e.g., 15–50 ml for blood, 1–10 ml for lymph, and 1–30 ml for spinal fluid correction), containing various xenobiotics, i.e. low-, medium- and high-molecular toxins, is withdrawn from the patient's body and directed into the flow tube 42 through the port 44. When dealing with the blood correction, a suitable anticoagulant such as, for example, heparin of approximately 500–900 units per kilogram depending on the patient's weight, is introduced into the blood either intravenously, prior to the withdrawal, or into the system 40.

The biological fluid first passes between the poles of the electromagnet 64, which generates an impulsive magnetic field having an intensity of about 30–50 mT. Such a magnetic field provides a so-called "shaking effect" for liberalization of the toxins contained in the biological fluid, namely tearing off those toxins which might have been adsorbed by the biological fluid proteins. This increases the efficiency of the whole process of separation by 15–20%.

The biological fluid then continues its flow into the portion 100 of the mixing assembly 66. Concurrently, the suspension 50 (generally, containing up to 100% of the paramagnetic particles) continuously flows into the portion 100 with a velocity of about 5–20 ml/min. The biological fluid and the suspension during their progressive flow in the direction D are together sequentially rotated in opposite directions and are, therefore, mixed. During the rotation, at least a part of the paramagnetic particles, due to their swelled, activated surfaces, adsorb the toxins contained in the biological fluid, thus obtaining a mixture containing the adsorptive and non-adsorptive paramagnetic particles and particle-free biological fluid. The mixture enters the portion 110 and passes through the magnetic field region between the magnets 72 and 74. As a result, the adsorptive and non-adsorptive particles adhere to the wire 112, and the particle-free biological fluid ensues from the portion 110. The particle-free biological fluid continues its flow in the direction D (through the filtering device 82, in the case of blood correction, wherein water is removed from the blood as described above), and enters the portion 120 of the trapper 96, wherein it again passes the magnetic field generated by the magnet 98. If there occasionally exist paramagnetic particles, either adsorptive or non-adsorptive, they are retained by the filler element 124. Then, the biological fluid ensuing from the portion 120 flows towards the inlet port 46 for running into the patient's body. If the sensor 99, accommodated as described above, detects an existence of any magnetic material within the biological fluid, it immediately operates the clamp 99*a* for interrupting the biological fluid flow into the patient's body.

Figure 6:
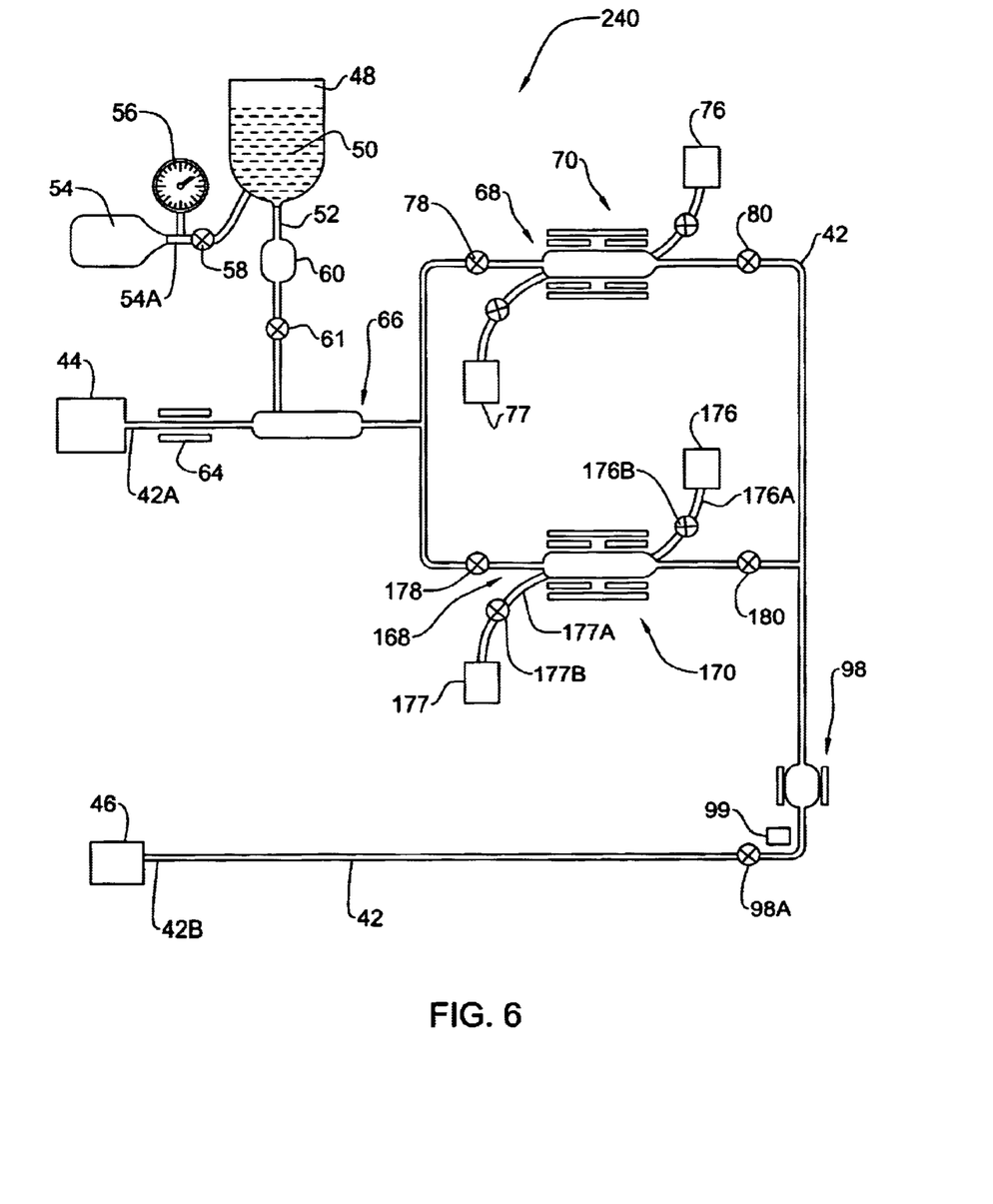
FIGS. 6 to 8 are schematic block diagrams illustrating the main components of three systems constructed and operated according to three more embodiments of the invention, respectively.

Reference is now made to FIG. 6 illustrating a system 140 according to another embodiment of the invention. The same reference numbers are used for indicating those constructional parts which are common to both the systems 40 and 140. The system 140 differs from the previously described system 40 in the provision of an additional separation assembly, generally designated 168. The assembly 168 is constructed and operative similar to the assembly 68 and comprises a magnetic mechanism 170 which is similar to the mechanism 70. The assembly 168 is connected through pipes 176a and 177a to an injector 176 and a vessel 177, respectively, which are put into operation for cleaning the assembly 168 after use. For this purpose, a pair of clamps 176b and 177b is mounted on the pipes 176a and 177a.

The assemblies 68 and 168 are accommodated in such a manner that the flow of the mixture ensuing from the mixing assembly 66 may be selectively directed into either one of the separation assemblies 68 and 168. To this end, an additional pair of clamps 178 and 180 is provided. During the operation of the separation assembly 68, the assembly 168 may be cleaned, and vice versa. This results in a non-interruptive process of correction.

Figure 7:
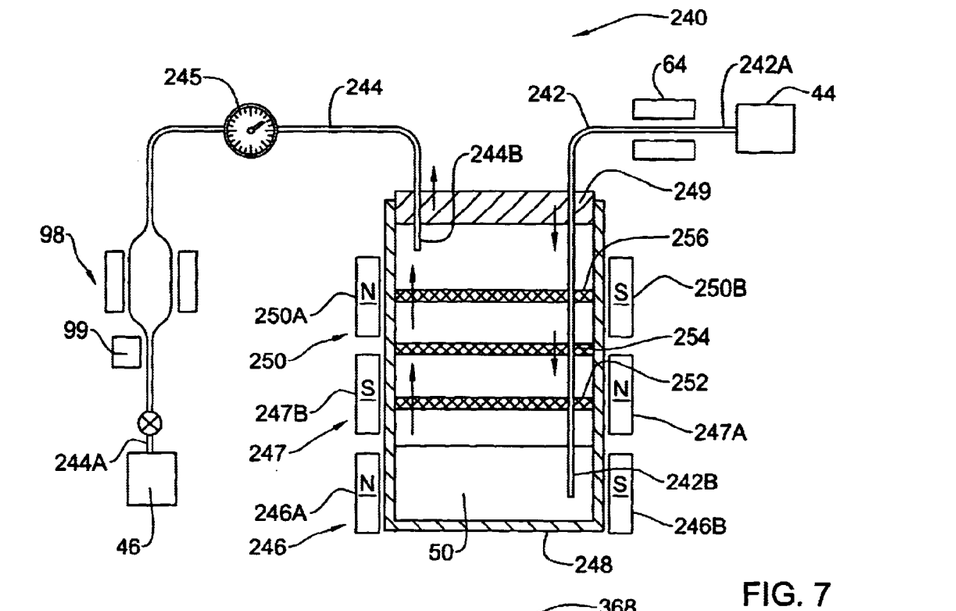

FIG. 7 illustrates a system, generally designated 240, constructed according to still another embodiment of the present invention. Similarly, in order to facilitate understanding, the same reference numbers indicate the common constructional parts of the systems 40, 140 and 240. The system 240 differs from the previously described system 40, 140 in that there is no flow of the suspension of the magneto-conductive material 50 into the flow line. Both the mixing and the separation are carried out within a vessel 248 containing the biocompatible suspension 50 disposed within a bottom region thereof. The vessel 248 is closed by a sealed cover 249. Additionally, the tube 42 of the system 40 is replaced by a pair of separate tubes 242 and 244. The tube 242 is connected at its one end 242a to the outlet port 44, while the tube 244 is coupled at its one end 244a to the inlet port 46, the ports 44 and 46 being attached to the corresponding location(s) on the patient's body, as described above. Free ends 242b and 244b of the tubes 242 and 244, respectively, are inserted into the vessel 248 through a pair of openings (not shown) provided in the cover 249. The end 242b is dipped into the suspension 50, while the end 244b is spaced therefrom.

It is appreciated that the blood containing various xenobiotics passes through the tube 242 and, upon ensuing therefrom through the end 242b, passes through the suspension 50 and then enters the end 244b of the tube 244. Three magnets 246, 247 and 250 are aligned in a spaced parallel relationship along a length of the vessel 248 so as to enclose the latter between their opposite poles 246a–246b, 247a–247b and 250a–250b. Three spaced parallel filler elements 252, 254 and 256 formed of paramagnetic or ferromagnetic material are aligned along the vessel 248 thereinside. Each of the filler elements is in the form of a lattice, or loosely laid material. The lowermost magnet 246 is continuously or periodically rotated so as to "shake up" the suspension 50 and, thereby, provide a movement of the paramagnetic particles within the bottom region of the vessel 248 for improving a mixing of the particles with the biological fluid and, therefore, the adsorbing process. Thus, a mixture containing the adsorptive and non-adsorptive particles and the particle-free biological fluid is provided. Subsequent passage of the mixture through the filler elements 252, 254 and 256 results in substantially all of the particles adhering to the elements 252–256. The particle-free biological fluid then enters the tube 244 and passes through the trapper 96 in the manner described above in respect of the system 40.

Figure 8:
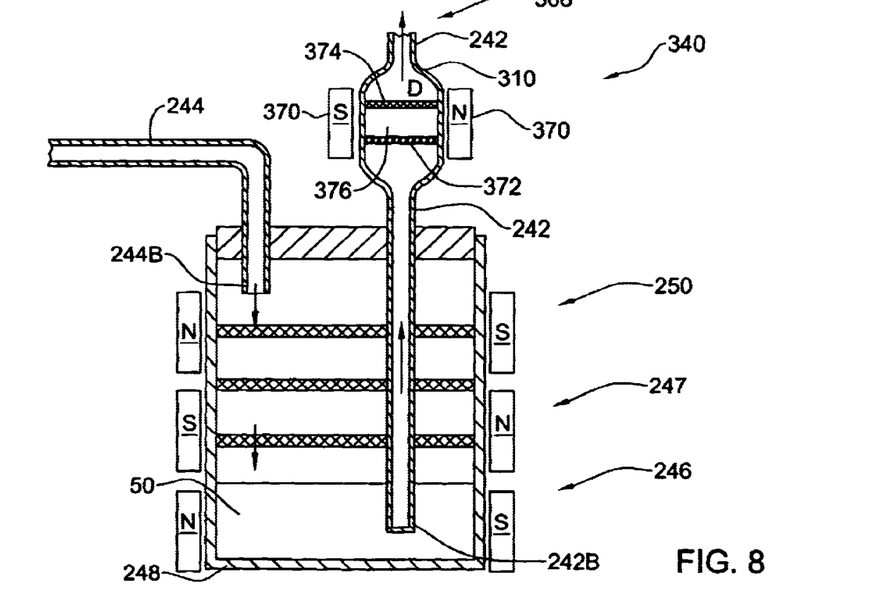

Turning now to FIG. 8, a system, generally designated 340, is illustrated. The system 340 is generally similar to the system 240 and additionally comprises a separation assembly 368 which is accommodated in the tube 242 upstream of the vessel 248. As shown, the assembly 368 is optionally formed of a thickened portion 310 of the tube 242 and enclosed by opposite poles of a permanent magnet 370. The magnet 370 may be either horseshoe or ring-shaped. Obviously, more magnets may be used being located in a spaced parallel relationship along a length of the portion 310 outside thereof. A pair of spaced parallel lattices 372 and 374 are mounted inside the portion 310 extending transverse to the flow direction D. Enclosed between the lattices is a magneto-conductive material 376 formed of paramagnetic or ferromagnetic particles with prevailing properties of hydrophobic colloid, rather than hydrophilic, while the particles 50 are, on the contrary, of prevailing hydrophilic properties. Hence, the material 376 is capable of adsorbing another kind of toxins such as, for example, bilirubin, holysterin or other poly-unsaturated fatty acids, which cannot be captured by hydrophilic adsorbents. It should be noted that this design is the most preferable for correction of the spinal fluid, as compared to those of the previous examples.

Following are two examples of the application of the system according to the invention for treating laboratory animals (dogs), and an example of treatment of the donor blood.

EXAMPLE 1

Lymph Fluid Correction

A dog weighing approximately 19 kg was treated. Its bilious duct was bandaged, and 3 days later the bilirubin (endo-toxin) level in its lymph fluid was found to be 160.6 micromole per liter, and in its blood 7.8 micromole per liter. Lymph-separation was applied to the dog for ten hours. Thereafter, the bilirubin levels in both its lymph fluid and blood were measured: in its lymph fluid it decreased to 24 micromole per liter, and in its blood, to the normal value.

EXAMPLE 2

Spinal Fluid Correction

A dog with the modeled cranial trauma (i.e., red spinal fluid) was treated. The spinal fluid separation was carried out with the speed of fluid circulation of 5–10 ml/min. The liquid solution in the magnetic particles' suspension was very small: 5– ml for 5 g of particles. After 2–3 hours, the color of the spinal fluid was changed from red to light, transparent.

EXAMPLE 3

Blood Correction

Data included in the following table illustrates the efficiency of the above described process of correction of one liter of the donor blood containing various toxins with concentration of about 100/ml. 50 m of 50% suspension of various kinds of magneto-conductive particles was employed.

| Magneto-conductive particles | Toxins | Removed amount (%) |
|---|---|---|
| | low-molec.: barbiturate | |
| Iron | | 90 |
| Carbon coated iron | | 85 |
| Zirconium based ion exchange resins | phosphor and phosphates | 90–95 |
| | med-molec.: | |
| Iron | vitamin $B_{12}$ | 67 |
| Carbon coated iron | | 54 |
| Silicone coated iron | | 75 |
| | high-molec.: | |
| Iron | free hemoglobin | 70 |
| Carbon coated iron | | 60 |
| Protein, carbon coated iron | | 90 |
| Dextran, carbon coated iron | | 80 |

Those skilled in the art will readily appreciate that many modifications and changes may be applied to the invention as described in the preferred embodiment thereof without departing from its scope defined in and by the appended claims.

What is claimed is:

1. A system for correcting a patient's biological fluid containing various low-, medium- and high-molecular toxins by interaction of the biological fluid with magneto-conductive particles, the system comprising:
   (i) an outlet means for attaching to the patient's body for substantially continuously withdrawing therefrom the biological fluid containing the various toxins;
   (ii) an inlet means for attaching to the patient's body for returning corrected biological fluid back into the patient's body;
   (iii) an extracorporeal flow line interconnected between the outlet and inlet means for passing therethrough, in a substantially continuous flow, a predetermined amount of the biological fluid substantially not exceeding 100 ml, the flow line comprising first and second flexible tubes and a sealed vessel with a plurality of magneto-conductive particles within its bottom region, the first tube being connected between the outlet means and the particles, the second tube being connected between the inlet means and a top region of the vessel, said magneto-conductive particles being capable of absorbing the toxins in the biological fluid, whereby said predetermined amount of biological fluid becomes mixed with said magneto-conductive particles to obtain a mixture of the biological fluid with said particles;
   (iv) a magnetic mechanism comprising a magnetic field source producing a magnetic field region within a flow of said mixture for retaining said magneto-conductive particles in said region from a flow of particle-free biological fluid to be returned into the patient's body through the inlet means; and
   (v) a pump assembly that provides the biological fluid flow through the flow line with a predetermined speed value.

2. The system according to claim 1, wherein said biological fluid to be treated is the patient's blood, the outlet and inlet means being adapted to be coupled to an artery and vein of the patient, respectively, to thereby enable the blood to flow through the flow line with its usual velocity of circulation within the patient's body.

3. The system according to claim 1, wherein said biological fluid to be treated is the patient's blood, the outlet and inlet means being adapted to be coupled to a vein of the patient.

4. The system according to claim 1, wherein said biological fluid to be corrected is the patient's lymph, the outlet means including a catheter adapted to be installed in the patient's large pectoral lympheduct at the place of its falling into the cava, the inlet means including a catheter adapted to be inserted into a jugular vein.

5. The system according to claim 1, wherein said biological fluid to be corrected is the patient's lymph, the outlet means including a catheter adapted to be installed into the patient's large pectoral lympheduct at the place of its falling into the cava, the inlet means including a catheter adapted to be inserted into a cubital vein.

6. The system according to claim 1, wherein said biological fluid to be corrected is the patient's lymph, the outlet and inlet means comprising a two-channel needle adapted to be inserted to the patient's large pectoral lympheduct at the place of its falling into the cava.

7. The system according to claim 1, wherein said biological fluid to be corrected is the patient's spinal fluid, the outlet means including a needle adapted to be inserted into the cistern through the cervical opening, and the inlet means including a needle adapted to be inserted between the $4^{th}$ and the $5^{th}$ lumbar vertebrae.

8. The system according to claim 1, wherein said biological fluid to be corrected is the patient's spinal fluid, the outlet and inlet means comprising a two-channel needle adapted to be inserted into the cistern through the cervical opening.

9. The system according to claim 1, wherein said biological fluid to be corrected is the patient's spinal fluid, the outlet and inlet means comprising a two-channel needle adapted to be inserted into the patient's spine between the $4^{th}$ and the $5^{th}$ lumbar vertebrae.

10. The system according to claim 1, wherein the magnetic mechanism also comprises an adhering means accommodated inside the flow line for adhering thereon the magneto-conductive particles, said adhering means being made of a paramagnetic or ferromagnetic material and creating the magnetic field region at least in the direction transverse to the flow direction of the mixture.

11. The system according to claim 10, wherein the adhering means includes a paramagnetic or ferromagnetic filler element installed inside the flow line within the magnetic field region.

12. The system according to claim 11, wherein the filler is in the form of a loosely laid wire.

13. The system according to claim 12, wherein said loosely laid wire is in the form of a barbed wire.

14. The system according to claim 12, wherein the wire has a varying diameter thereof and a varying laying density within the magnetic field region.

15. The system according to claim 10, wherein the magnetic field source and the adhering means are constituted by at least one permanent magnet accommodated inside the flow line.

16. The system according to claim 1, wherein the magnetic field source comprises at least one permanent magnet mounted outside the flow line and proximate thereto.

17. The system according to claim 16, wherein said at least one permanent magnet is in the form of a substantially flat plate.

18. The system according to claim 16, wherein said at least one permanent magnet is ring-shaped for surrounding the flow line.

19. The system according to claim 16, wherein opposite poles of each magnet are connected by a cover plate formed of a magnetic soil material.

20. The system according to claim 1, wherein said magnetic mechanism also comprises a wire wound on an outer surface of the flow line within the magnetic field region.

21. The system according to claim 1, and also comprising a control means coupled to the flow line and to the magnetic mechanism for operating thereof.

22. The system according to claim 1, wherein said biological fluid to be corrected is the patient's blood, the system also comprising a filtering means for removing water from the blood.

23. The system according to claim 22, wherein the filtering means includes at least one semipermeable membrane.

24. The system according to claim 22, wherein the filtering means includes adsorbent material formed of hydrolyzed starch polymer.

25. The system according to claim 22, wherein said filtering means is accommodated in the flow path of the biological fluid containing the various toxins.

26. The system according to claim 22, wherein said filtering means is accommodated in the flow path of the particle-free biological fluid.

27. The system according to claim 1, wherein the magneto-conductive particles have activated porous surfaces.

28. The system according to claim 27, wherein said particles are made of iron.

29. The system according to claim 27, wherein said particles are made of iron oxide.

30. The system according to claim 27, wherein said particles are made of carbon coated iron.

31. The system according to claim 27, wherein said particles are made of silicone coated iron.

32. The system according to claim 27, wherein said particles are made of aluminum coated iron.

33. The system according to claim 27, wherein said particles are made of dextran coated iron.

34. The system according to claim 27, wherein each of said magneto-conductive particles has a protective layer coating containing protein or the patient's blood.

35. A system, for correcting a patient's biological fluid containing various low-, medium- and high-molecular toxins by interaction of the biological fluid with magneto-conductive particles, the system comprising:

(i) an outlet means for attaching to the patient's body for substantially continuously withdrawing therefrom the biological fluid containing the various toxins;

(ii) an inlet means for attaching to the patient's body for returning corrected biological fluid back into the patient's body;

(iii) an extracorporeal flow line interconnected between the outlet and inlet means for passing therethrough, in a substantially continuous flow path, a predetermined amount of the biological fluid substantially not exceeding 100 ml, the extracorporeal flow line comprising a mixing means located in the flow path of the biological fluid containing the various toxins, said mixing means being adapted to thereby provide mixing of the biological fluid with a plurality of magneto-conductive particles capable of adsorbing said toxins for obtaining a mixture of the biological fluid with the magneto-conductive particles during operation of said system; and (iv) a magnetic mechanism comprising a magnetic field source producing a magnetic field region within a flow of said mixture for retaining the magneto-conductive particles in said region from a flow of particle-free biological fluid to be returned into the patient's body through the inlet means during operation of said system.

36. The system according to claim 20, wherein said flow line is in the form of a flexible tube.

37. The system according to claim 35, and also comprising a vessel adapted to contain magneto-conductive particles, said vessel being coupled to the flow line through a pipe.

38. The system according to claim 37, wherein said vessel contains a suspension of said magneto-conductive particles.

39. The system according to claim 38, wherein the magneto-conductive particles have activated porous surfaces.

40. The system according to claim 39, wherein said particles are made of at least one of the following iron, iron oxide, carbon coated iron, silicone coated iron, aluminum coated iron, and dextran coated iron.

41. The system according to claim 39, wherein each of said magneto-conductive particles has a protective layer coating containing protein or the patient's blood.

42. The system according to claim 35, and also comprising a feeding means adapted to substantially continuously feed the magneto-conductive particles into the flow line.

43. The system according to claim 42, wherein said feeding means comprises a pump coupled to the vessel for supplying air thereto so as to provide an excessive pressure within the vessel.

44. The system according to claim 35, and also comprising a pump assembly that provides the biological fluid flow through the flow line with a predetermined speed value.

45. The system according to claim 44, wherein said biological fluid to be corrected is the patient's lymph, the speed of circulation being about 1–10 ml/min.

46. The system according to claim 44, wherein said biological fluid to be corrected is the patient's spinal fluid, the speed of circulation being about 1–30 ml/min.

47. The system according to claim 35, wherein said flow line has an inside region thereof adapted for location of the magneto-conductive particles therewithin so as to be in a flow path of the biological fluid containing the various toxins flowing towards the magnetic field region.

48. The system according to claim 35, wherein the mixing means comprises a multi-threaded worm mechanism.

49. The system according to claim 35, wherein the mixing means comprises a magnetic mechanism having displaceable opposite magnetic poles.

50. The system according to claim 35, wherein the magnetic mechanism also comprises an adhering means accommodated inside the flow line adapted to adhere thereon the magneto-conductive particles, said adhering means being made of a paramagnetic or ferromagnetic material and creating the magnetic field gradient at least in the direction transverse to the flow direction of the mixture.

51. The system according to claim 35, wherein the magnetic field source comprises at least one permanent magnet mounted outside the flow line and proximate thereto.

52. The system according to claim 35, comprising at least one permanent magnet accommodated inside the flow line, said at least one permanent magnet serving as the magnetic field source and as an adhering means adapted for adhering thereon the magneto-conductive particles.

53. The system according to claim 35, wherein said biological fluid to be corrected is the patient's blood, the system also comprising a filtering means for removing water from the blood.

54. The system according to claim 35, wherein said biological fluid to be treated is the patient's blood, the outlet and inlet means being adapted to be coupled to an artery and vein of the patient, respectively, to thereby enable the blood to flow through the flow line with its usual velocity of circulation within the patient's body.

55. The system according to claim 35, wherein said biological fluid to be treated is the patient's blood, the outlet and inlet means being adapted to be coupled to a vein of the patient.

56. The system according to claim 35, wherein said biological fluid to be corrected is the patient's lymph, the outlet means including a catheter adapted to be installed in the large pectoral lympheduct at the place of its falling into the cava, the inlet means including a catheter adapted to be inserted into a jugular vein.

57. The system according to claim 35, wherein said biological fluid to be corrected is the patient's lymph, the outlet means including a catheter adapted to be installed into the large pectoral lympheduct at the place of its falling into the cava, the inlet means including a catheter adapted to be inserted into a cubital vein.

58. The system according to claim 35, wherein said biological fluid to be corrected is the patient's lymph, the outlet and inlet means comprising a two-channel needle adapted to be inserted to the large pectoral lympheduct at the place of its falling into the cava.

59. The system according to claim 35, wherein said biological fluid to be corrected is the patient's spinal fluid, the outlet means including a needle adapted to be inserted into the cistern through the cervical opening, and the inlet means including a needle adapted to be inserted between the $4^{th}$ and the $5^{th}$ lumbar vertebrae.

60. The system according to claim 35, wherein said biological fluid to be corrected is the patient's spinal fluid, the outlet and inlet means comprising a two-channel needle adapted to be inserted into the cistern through the cervical opening.

61. The system according to claim 35, wherein said biological fluid to be corrected is the patient's spinal fluid, the outlet and inlet means comprising a two-channel needle adapted to be inserted into the patient's spine between the $4^{th}$ and the $5^{th}$ lumbar vertebrae.

62. The system according to claim 35, wherein said magnetic mechanism also comprises a wire wound on an outer surface of the flow line within the magnetic field region.

63. The system according to claim 35, and also comprising a control means coupled to the flow line and to the magnetic mechanism for operating thereof.

* * * * *